United States Patent [19]
Perlman

[11] Patent Number: 5,851,613
[45] Date of Patent: Dec. 22, 1998

[54] ABSORBENT FILTER PAPER STICK

[75] Inventor: Daniel Perlman, Arlington, Mass.

[73] Assignee: Brandeis University, Waltham, Mass.

[21] Appl. No.: 810,252

[22] Filed: Mar. 3, 1997

[51] Int. Cl.⁶ ..................................... B32B 9/00
[52] U.S. Cl. ........................ 428/36.3; 428/32; 428/34.2; 428/57; 428/62; 428/121; 428/124; 428/171; 428/192; 428/401; 428/913; 604/1; 604/2; 15/104.94
[58] Field of Search ................................ 728/57, 62, 401, 728/913, 124, 192, 121, 194, 171, 34.2, 32, 36.3; 604/375, 1, 2; 15/104.94

[56] References Cited

U.S. PATENT DOCUMENTS

| | | | |
|---|---|---|---|
| 2,137,958 | 11/1938 | Stephan | 15/225 |
| 2,813,286 | 11/1957 | Strader | 15/118 |
| 3,542,025 | 11/1970 | Gustafson | 604/1 |
| 3,591,885 | 7/1971 | Fritzen | 15/210.1 |
| 3,609,789 | 10/1971 | Slater | 15/104.94 |
| 3,671,993 | 6/1972 | Smedstad | 15/211 |
| 4,855,108 | 8/1989 | Masuda et al. | 422/56 |
| 5,214,821 | 6/1993 | Burrow et al. | 15/210.1 |
| 5,229,181 | 7/1993 | Daiber et al. | 428/58 |
| 5,681,437 | 10/1997 | Black et al. | 204/456 |

*Primary Examiner*—Bruce H. Hess
*Assistant Examiner*—Abraham Bahta
*Attorney, Agent, or Firm*—Lyon & Lyon LLP

[57] ABSTRACT

An essentially homogeneous, water-resistant, water-absorbent rod, containing a cohesive spiral winding of water-resistant, water-absorbent sheet material, in which the rod can absorb at least 50% by weight of water when placed in water at 23° C. for one minute. Methods for fabricating and using this rod are also described.

17 Claims, No Drawings

ABSORBENT FILTER PAPER STICK

BACKGROUND OF THE INVENTION

This invention relates to the structure, fabrication, and use of an absorbent device in the form of an essentially homogeneous stick, i.e., rod, which is formed from a permeable and absorbent sheet material, preferably filter paper, by mechanically winding the sheet material upon itself (similar in style to a paper lollipop stick) to produce a structure which serves as an absorbent receptacle device for liquids, and as a carrier device for liquids, pastes, gels, and solid materials.

There are many prior art devices which can be generally described as absorbent sticks, rods and cylinder-shaped absorbent instruments ranging from the common cotton-tipped swab to surgical sponges and absorbent tampons. Considering the sub-group of absorbent swab devices which contain spirally wound or otherwise wrapped absorbent sheet materials, Smedstad, U.S. Pat. No. 3,671,993 describes the use of moisture-absorbing material, wound around a semi-rigid core and secured with string-like encirclements to form an absorbent rod used to dry test tubes. A number of other swab-type devices contain rolled up or wrapped absorbents. Stepan, U.S. Pat. No. 2,137,958 describes a rolled up paper mop whose length can be gradually shortened over the mop's lifetime, and which is held together by a strong external reinforcement band. Gustafson, U.S. Pat. No. 3,542,025 describes a medical swab which includes a spirally wound web of non-woven material such as cotton, bonded to the end portion of a stick. Fritzen, U.S. Pat. No. 3,591,885 describes an absorbent swab consisting of a wad of absorbent material covered by a porous sock or envelope which, in turn, is secured to a handle. Burrow et al., U.S. Pat. No. 5,214,821 describe a "low contamination" swab having a tubular knit material helically wrapped around, and extending beyond the end of a handle to a tip, and then wrapped in reverse helix to a termination point on the handle.

SUMMARY OF THE INVENTION

This invention features a coherent and essentially homogeneous absorbent rod (essentially uniform in structure from its center to its exterior surface) which can be assembled from a single absorbent sheet, such as a wood pulp filter paper or cotton linter filter paper sheet. The absorbent sheet is spirally wound upon itself, and cohered using one or more fabrication conditions which favor cohesion, including moisture, pressure, and/or heat. As an option, an adhesive may be added during or after fabrication of the rod to improve the resistance of the rod to unwinding during sustained immersion in water or other liquid, particularly hot or boiling water. The absorbent sheet material and adhesive are selected to be at least water-resistant if not waterproof. By the term "water-resistant" is meant that the material and adhesive show no visible structural deterioration (such as shedding of paper fiber or loss of adhesive contact between the adhesive and the absorbent sheet) during immersion in water at 23° C. for a period of at least 10 minutes. Water-resistance of the adhesive need not substantially reduce the transfer rate of water and other liquids into and out from the porous rod, providing that the adhesive is used at a minimum but sufficient application rate to achieve permanent adhesion of the absorbent sheet material to itself. The adhesive is also similarly resistant to common organic solvents such as alcohols, and caustic agents such as dilute HCl and dilute NaOH solutions utilized in clinical and research laboratories. Such resistance allows contact with these substances without degradation of the adhesive. There is no need for any structural component besides the absorbent sheet material for initiating the rod assembly process (e.g., there is no requirement for a center core). Similarly, there is no need for any structural component for completing the rod assembly process (such as wrapping bands, ligatures or an outer covering for structural integrity). Furthermore, the rod serves as its own handle. Thus, in comparison to the absorbent rods of Burrow and Smedstad for example, the presently invented absorbent rod is simpler and less inexpensive to manufacture, and functions without a separate handle or any interference by external wrappings and ligatures.

It is widely known and appreciated that small disposable absorbent devices such as cotton-tipped swabs (also known as Q-tips) are available for applying as well as absorbing and removing small amounts of liquids such as water, solvents, lubricants, medications and the like. The use of loose cotton fiber absorbent-containing devices such as the Q-tip in lint-free industrial and research environments can be problematic. Accordingly, lint-free specialty-absorbent devices such as urethane foam-tipped swabs are available for this purpose, but are typically expensive. While inexpensive and essentially lint-free soft paper wipes (e.g., Kimwipes® manufactured by Kimberly Clark, Inc., Neenah, Wis.) are widely used in clinical and research laboratories, it is difficult to utilize these non-rigid sheet materials for delivering or removing substances from inside a container, particularly a narrow container such as a test tube, flask, or similar container. Furthermore, the liquid absorption capacity of such paper wipes is very limited. Accordingly, it would be useful to construct a rigid or semi-rigid, inexpensive and lint-free absorbent device, generally in the form of a stick, having an ample absorption capacity. Preferably, the stick would be sufficiently rigid to serve as its own handle, and should withstand immersion in a liquid such as hot water without losing integrity of structure.

Accordingly, in one aspect, the present invention features an essentially homogeneous, water-resistant and water-absorbent rod which includes a cohesive spiral winding of water-resistant, water-absorbent sheet material. The rod can absorb at least 50% by weight of water when placed in water at 23° C. for one minute.

In one preferred embodiment, the rod further contains a water-resistant adhesive agent which prevents unwinding of the sheet material during sustained immersion of the rod in water and other liquids.

In other preferred embodiments, the rod includes a sheet material selected from the group consisting of wood pulp filter paper and cotton linter filter paper; the sheet material is substantially lint-free; the rod measures between approximately 0.05 and 0.50 inches in diameter and between 1.0 and 10 inches in length.

In a related aspect, the invention features an essentially homogeneous, water-resistant and water-absorbent rod which includes a spiral winding of water-resistant, water-absorbent sheet material, and a water-resistant adhesive agent which prevents unwinding of the sheet material during sustained immersion of the rod in water and other liquids. The rod can absorb at least 50% by weight of water when placed in water at 23° C. for one minute.

In a preferred embodiment, the above rod includes a sheet material selected from the group consisting of wood pulp filter paper and cotton linter filter paper.

In other preferred embodiments, the rod is also substantially lint-free; the rod measures between approximately 0.05 and 0.50 inches in diameter and between 1.0 and 10 inches in length; the rod includes a water-resistant adhesive agent which is also resistant to common organic solvents and caustic agents; the water-resistant adhesive agent is selected from the group consisting of vinyl acetate-ethylene copolymer aqueous emulsion adhesives, acrylic adhesives, and rubber adhesives.

In another aspect, the present invention features a method for removing a quantity of liquid from a container. The method includes the steps of placing any one of the above-described rods in contact with the liquid in the container to absorb the liquid, and then removing the rod carrying the liquid from the container.

In still another aspect, a method is provided for delivery of a quantity of material to a receiving medium or surface. The method includes the steps of placing any one of the above rods carrying the material into contact with the receiving medium or surface, and then removing the rod from the receiving medium or surface after an interval of time which has allowed such delivery to occur.

In a preferred embodiment of the above delivery method, the material is selected from the group including food, food additive, pharmaceutical, laboratory chemical, cosmetic, cleaning, lubricating, home maintenance, vehicular maintenance, and repair materials.

In other preferred embodiments, the receiving medium or surface is selected from the group consisting of edible and non-edible, animate and inanimate, aqueous and non-aqueous, and liquid and solid media and surfaces; the material is a food sweetener and the receiving medium is a beverage; the material is a cosmetic cream and said receiving medium is the human face;

In yet another aspect of the present invention, a method is provided for fabricating an essentially homogeneous, water-resistant, water-absorbent rod. The method includes the steps of providing a sized portion of water-resistant, water-absorbent material, in which the sheet material is selected from the group consisting of wood pulp filter paper and cotton linter filter paper. The sized portion of sheet material is mechanically wound upon itself in a spiral geometry, using heat, pressure, and/or moisture to cohere the sheet material.

In a related aspect, the above method further includes the step of adding a water-resistant adhesive during or after the mechanical winding step to prevent possible unwinding of the sheet material if the rod is immersed in water and other liquids.

In a preferred embodiment, the sized portion of the sheet material is between 5 and 20 inches in length, and the basis weight of the material is between 15 and 30 pounds per 3000 square feet of material.

The present invention features an absorbent blotting/applicator rod or stick (hereinafter termed "blot-stick") which typically has a solid cylindrical geometry with a length of between 1 and 10 inches, and a diameter of between 0.05 and 0.50 inches. The blot-stick is fabricated from a porous absorbent material in the form of a sized portion of sheet, typically 5–20 inches long (hereinafter absorbent sheet), preferably filter paper, which is substantially free of mobile sizing materials (such as starch) found in conventional paper. Mobile sizing material is defined as glutinous material which is at least partially diffusible or soluble in hot water, and is used for either filling the pores within a conventional paper sheet, improving cohesion within the paper, i.e., holding the paper fibers together, or reducing the penetration of the paper by liquids. Typical prior art paper lollipop sticks are fabricated from a bond-type or other conventional lignin-free, virgin wood pulp paper (hereinafter termed conventional paper) containing one or more sizing materials which help the paper cohere in the presence of moisture, heat, and pressure introduced in the winding process used to form the stick. Commercially manufactured paper lollipop sticks may also be treated with paraffin wax, further reducing water absorption and helping the stick survive in the mouth.

By contrast, a typical sheet material useful in the present invention is absorbent (see below), such as "wet-strength" filter paper (paper which is resistant to tearing when wet), having a basis weight of between 15 and 30 pounds (weight per 3000 square feet of paper), such as commercially available "wet crepe coffee filter stock". Such wet crepe filter paper fabricated from 100% virgin fiber wood pulp is commercially available from the Scott Paper Company (Philadelphia, Pa.). The weight density and water absorbency of paper blot-sticks of the present invention (fabricated from wet crepe coffee filter stock) were compared with those of conventional paper lollipop sticks. All of the sticks which were tested and compared had a range of diameters between 0.10 to 0.20 inches, and were commercially manufactured using commercial paper sheet winding machinery (Setterstix, Inc., Cattaraugus, N.Y.) employing heat, pressure and moisture to cohere the paper as it is being wound. Typical blot-sticks of the present invention have a density of between 0.45–0.55 g/cm$^3$ while conventional paper lollipop sticks manufactured on the same equipment had a density of between 0.80–0.95 g/cm$^3$. This substantial difference in density is not surprising, given that the filter paper used to fabricate the blot-sticks contains a substantial proportion of void volume (based upon tests by Applicant showing that the blot-sticks can absorb between 55% and 75% by volume water). With regard to water absorbency, the difference between the blot-sticks and the conventional paper lollipop sticks was dramatic and surprising. For absorbency testing and for purposes of definition in the present invention, materials and devices were floated in distilled water for 1 minute at 23° C., and then briefly wiped free of surface water. While conventional paper sticks showed only between a 3% and 5% weight gain, blot sticks showed between a 150% and 180% weight gain. In many instances, a 1 gram blot-stick absorbed nearly 2 grams of water. Thus, on a weight basis (and for purposes of definition in the present invention), paper blot-sticks when placed in water at room temperature, 23° C., can absorb at least 50% by weight of water in one minute, and typically absorb 100%–200% by weight of water in one minute, or about 25–50-fold more water than conventional paper sticks.

Other features also help in distinguishing the present invention from prior art devices. For example, the blot-stick rod described herein is essentially homogeneous in its structure (essentially 100% absorbent sheet material), while the device of Smedstad contains and requires a central core for its fabrication, and ligatures for holding it together. In the process of developing the present invention, Applicant discovered that when a fibrous sheet material such as filter paper is rolled up under pressure and heat (moisture also being helpful for cohesion of many materials), the juxtapositioned paper fibers in the spiral winding can interlock to prevent the paper from unwinding. The blot-stick is preferably fabricated from a porous absorbent material which is essentially lint-free (i.e., as recognized in the art, the material does not shed a significant proportion (less than 1% by weight) of its paper fiber content under non-abrasive conditions of routine use). The blot-stick also contains little (less than 1% by weight) measurable extractable substances which would constitute chemical contaminants. One suitable absorbent material for use in the present invention is filter paper sheet qualified for laboratory use or for potable water filtration (Whatman No. 1 filters, Whatman, Inc., Fairfield, N.J.). Such filters are made from virgin wood pulp, 100% cotton linters, or blends thereof. If the blot-stick is to be used in contact with food and/or drug materials, its absorbent paper must be FDA-qualified, such as wet crepe coffee filter stock manufactured by the Scott Paper Company.

At first glance, typical blot-sticks of the present invention resemble paper lollipop sticks or paper stick handles used in fabricating cotton Q-tip swabs. In fact, blot-sticks have been manufactured using the same machinery and conditions similar to those used to form lollipop sticks. The manufacturing process as commercially described for lollipop sticks (Setterstix, Inc., Cattaraugus, N.Y.), involves rolling a paper sheet upon itself under a moving, tensioned rubber belt, and bonding the paper to itself with moisture, pressure and/or heat. The final diameter of a paper stick formed by this process is determined by the thickness and length of the paper sheet being rolled, and by the pressure which the moving belt transmits to the paper stick as it is being formed. A blot-stick formed by this process can be used like a cotton swab except that the stick is designed to be more absorbent and is lint-free. As such, it can also be used as a laboratory clean-room swab. Unlike the swab structure however, the entire length of the device rather than just the tip can be used as an blotting or absorbent device for water and other aqueous liquids or solvents. With the entire length of the stick being absorbent, it is ideal for wiping the inside of a test tube, microcentrifuge tube, or the smooth inside surface of any other container. The blot-stick can also be used as a cleaning device to reach into corners and edges such as on mounted optical lenses, electronics devices, and the like. Alternatively, the device can be employed as an application or delivery means for water-soluble or organic solvent-soluble substances, lubricants and the like. The device is preferably manufactured from one structural component (such as filter paper) in a single operation, and is designed to be simpler and less expensive than a two-piece swab (e.g., an absorbent material mounted on the end of a stick), or the absorbent rod of Smedstad having a core and ligature structure.

While rolled paper sticks have been fabricated for many decades and used in the food and pharmaceutical industries as handles on products ranging from lollipops to cotton swab applicators, these paper handles are fabricated from substantially non-absorbent paper sheet material such as commercially available bond paper (typically 15–30 pound basis weight, as defined above). In fact, water absorbency is undesirable because many of the uses for these handles require that they remain stiff and intact in the presence of moisture (e.g., a lollipop in ones mouth). Accordingly, the use of absorbent sheet material taught in the present invention, runs contrary to the type of sheet material considered useful in the fabrication of paper handles. Furthermore, the use of heat and moisture in the fabrication of the prior art paper handles, serves to mobilize desirable sizing materials (e.g., starches) found in conventional paper, to cement together the adjacent layers of paper. However, for use in the present invention, the presence of any diffusible sizing material (in a filter paper, for example) would be contraindicated because in the presence of moisture, it could be mobilized and contaminate either a clean surface or a chemically pure or defined liquid. In summary, as described, the blot-stick is used as a chemically clean absorbent blotting device or conversely, as a carrier and applicator device for water and other liquids, creams, powders, lubricants, medications, and solvents, and the like. The absorbent paper used for fabricating the blot-stick preferably has little to no surface lint so that the stick leaves little or no lint on clean contacted surfaces.

To improve the resistance of the blot-stick to immersion in a variety of liquids, a water-resistant, and preferably solvent-resistant adhesive can be added to the absorbent sheet material during or after the sheet-rolling process. To qualify as solvent-resistant, the dried adhesive cannot dissolve in common alcohols or in common aromatic and chlorinated solvents, e.g., ethanol, toluene, and trichloroethane. After application and drying of the adhesive in the absorbent sheet material, it is also preferred that the adhesive survive at least brief exposure to boiling water (survival being defined as resistance of the blot-stick to unwinding). After fabricating a typical blot-stick by sheet-rolling ten inch lengths of 16–20 pound filter paper (100% virgin wood pulp-derived filter paper from the Scott Paper Company, Philadelphia, Pa.), Applicant has spray-applied aqueous emulsion adhesives such as vinyl acetate-ethylene (VAE) copolymer emulsions (e.g., Airflex 465 emulsion, manufactured by Air Products and Chemicals, Inc., Allentown, Pa.). For spraying purposes, this particular adhesive (which contains 66% by weight solids) has been diluted with between one and four volumes of water. The adhesive sets rapidly and dries clear. The dry adhesive has excellent mechanical stability, water resistance, and resists most common solvents such as alcohols, glycols, petroleum-based hydrocarbon-type solvents, and the like. At the same time, the adhesive (having been applied as a discontinuous and typically diluted spray-coating) has a negligible affect on water and solvent absorption rates.

Other embodiments are within the following claims.

I claim:

1. An essentially homogeneous, water-resistant, water-absorbent rod comprising a cohesive spiral winding of water-resistant, water-absorbent sheet material, wherein said rod can absorb at least 50% by weight of water when placed in water at 23° C. for one minute.

2. The rod of claim 1 further containing a water-resistant adhesive agent which prevents unwinding of said sheet material during sustained immersion of said rod in water.

3. The rod of claim 1 wherein said sheet material is selected from the group consisting of wood pulp filter paper and cotton linter filter paper.

4. The rod of claim 1 wherein said sheet material is substantially lint-free.

5. The rod of claim 1, measuring between approximately 0.05 and 0.50 inches in diameter and between 1.0 and 10 inches in length.

6. An essentially homogeneous, water-resistant, water absorbent rod comprising a spiral winding of water-resistant, water-absorbent sheet material, and a water-resistant adhesive agent which prevents unwinding of said sheet material during sustained immersion of said rod in water, wherein said rod can absorb at least 50% by weight of water when placed in water at 23° C. for one minute.

7. The rod of claim 6 wherein said sheet material is selected from the group consisting of wood pulp filter paper and cotton linter filter paper.

8. The rod of claim 6 wherein said rod is also substantially lint-free.

9. The rod of claim 6, measuring between approximately 0.05 and 0.50 inches in diameter and between 1.0 and 10 inches in length.

10. The rod of claim 6, wherein said water-resistant adhesive agent is also resistant to alcohols, glycols, and petroleum-based hydrocarbon solvents and to dilute HCl and NaOH solutions.

11. The rod of claim 6 wherein said water-resistant adhesive agent is selected from the group consisting of vinyl acetate-ethylene copolymer aqueous emulsion adhesives, acrylic adhesives, and rubber adhesives.

12. The rod of claim 1, wherein said sheet material contains less than one percent by weight extractable substances.

13. The rod of claim 12, wherein said extractable substances comprise mobile sizing materials.

14. The rod of claim 1, wherein said cohesive spiral winding is held by interlocking of paper fibers in said spiral winding.

15. The rod of claim 1, wherein said cohesive spiral winding is held without the use of an adhesive.

16. The rod of claim 6, wherein said sheet material contains less than one percent by weight extractable substances.

17. The rod of claim 16, wherein said extractable substances comprise mobile sizing materials.

* * * * *